(12) United States Patent
Murata et al.

(10) Patent No.: US 6,313,321 B1
(45) Date of Patent: Nov. 6, 2001

(54) PROCESS FOR PREPARING β-HYDROXY-γ-BUTYROLACTONES AND β-(METH)ACRYLOYLOXY-γ-BUTROLACTONES

(75) Inventors: Naoshi Murata; Kunihiko Sakano; Tetsuya Ikemoto, all of Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/603,842

(22) Filed: Jun. 26, 2000

Related U.S. Application Data

(63) Continuation of application No. PCT/JP98/05840, filed on Dec. 24, 1998.

(30) Foreign Application Priority Data

Dec. 15, 1997 (JP) ..................................................... 9-357715

(51) Int. Cl.⁷ ....................... C07D 307/04; C07D 307/12
(52) U.S. Cl. ........................................... 549/313; 549/318
(58) Field of Search ..................................... 549/313, 318

(56) References Cited

U.S. PATENT DOCUMENTS 4,200,582   4/1980   Distler et al. .

4,968,817   11/1990   Brima .

FOREIGN PATENT DOCUMENTS

| 54-95558 | 7/1979 | (JP) . |
| 2-129645 | 5/1990 | (JP) . |
| 10-212283 | 8/1998 | (JP) . |

*Primary Examiner*—T. A. Solola
(74) *Attorney, Agent, or Firm*—Oblon, Spivak, McClelland, Maier & Neustadt, P.C.

(57) ABSTRACT

The present invention provides a process for preparing β-hydroxy-γ-butyrolactone or β-methyl-β-hydroxy-γ-butyrolactone represented by the formula (1):

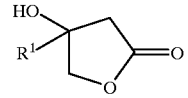

(1)

wherein $R^1$ is hydrogen or methyl, which entails a) cyanating glycidol or 2-methyl-2,3-epoxypropanol, b) hydrolyzing the product of step a), and c) lactonizing the product of step b).

30 Claims, No Drawings

PROCESS FOR PREPARING β-HYDROXY-γ-BUTYROLACTONES AND β-(METH)ACRYLOYLOXY-γ-BUTROLACTONES

This application is a continuation of PCT/JP98/05840 filed Dec. 24, 1998.

BACKGROUND OF THE INVENTION

1. Field of the Invention

The present invention relates to a process for preparing β-hydroxy-γ-butyrolactone and β-methyl-β-hydroxy-γ-butyrolactone (hereinafter referred to as "β-hydroxy-γ-butyrolactones"), and a process for preparing β-(meth)acryloyloxy-γ-butyrolactone and β-methyl-β-(meth)acryloyloxy-γ-butyrolactone (hereinafter referred to as "β-(meth)acryloyloxy-γ-butyrolactones") which are useful as a constituent component monomer of paints, adhesives, sticking agents, and resins for ink, for example.

2. Description of the Background

β-hydroxy-γ-butyrolactones, which are used as a precursor of β-(meth)acryloyloxy-γ-butyrolactones, for example, may be prepared by reacting glycidol with carbon monoxide at high temperature under high pressure using a noble metal as a catalyst (U.S. Pat. No. 4,968,817) and by lactonizing an epoxidized product, obtained by reacting 3-butenoic acid with hydrogen peroxide in the presence of a platinum catalyst, after hydrating the epoxidized product (Angew. Chem., Int. Ed. Eng. 994–1000 (1966)). However, both methods are attended by a high risk of explosion.

Due to this risk, it is difficult to industrially prepare β-hydroxy-γ-butyrolactones, hence, β-(meth)acryloyloxy-γ-butyrolactones have never been producing industrially using these compounds as a raw material, despite the expected use for various purposes.

Therefore, it has been considered desirable to develop a process for preparing β-hydroxy-γ-butyrolactones in a safe and simple manner, as well as a process for preparing β-(meth)acryloyloxy-γ-butyrolactones.

SUMMARY OF THE INVENTION

Accordingly, it is an object of the present invention to provide a process for preparing β-hydroxy-γ-butyrolactones in a safe and simple manner, as well as a process for preparing β-(meth)acryloyloxy-γ-butyrolactones, which are useful as a constituent component monomer of paints, adhesives, sticking agents, and resins for ink, for example, using β-hydroxy-γ-butyrolactones obtained by the above process.

In particular, the present invention provides a process for preparing corresponding β-hydroxy-γ-butyrolactone or β-methyl-β-hydroxy-γ-butyrolactone represented by the formula (1):

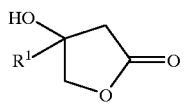

(1)

wherein $R^1$ represents a hydrogen atom or a methyl group, which entails cyanating glycidol or 2-methyl-2,3-epoxypropanol, followed by hydrolysis and then lactonization.

The present invention also provides a process for preparing corresponding the β-(meth)acryloyloxy-γ-butyrolactone or β-methyl-β-(meth)acryloyloxy-γ-butyrolactone represented by the formula (2):

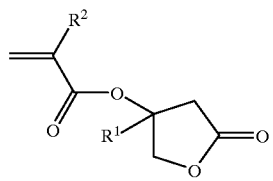

(2)

wherein $R^1$ and $R^2$ independently represent a hydrogen atom or a methyl group, which entails preparing β-hydroxy-γ-butyrolactone or β-methyl-β-hydroxy-γ-butyrolactone by the above process, and then reacting the resulting β-hydroxy-γ-butyrolactone or β-methyl-β-hydroxy-γ-butyrolactone with (meth)acrylic acid chloride, (meth)acrylic acid or (meth)acrylic ester.

DETAILED DESCRIPTION OF THE PREFERRED EMBODIMENTS

In the process of the present invention, glycidol or 2-methyl-2,3-epoxypropanol is cyanated, first, in order to prepare β-hydroxy-γ-butyrolactone or β-methyl-β-hydroxy-γ-butyrolactone represented by the formula (1), which are referred to as β-hydroxy-γ-butyrolactones. The process of cyanation is not specifically limited, but cyanation is usually performed by reaction with hydrocyanic acid or a hydrocyanate.

The process of cyanating using hydrocyanic acid includes, for example, reacting glycidol or 2-methyl-2,3-epoxypropanol with hydrocyanic acid in the presence of a basic catalyst. The basic catalyst used in the reaction is not specifically limited, but an inorganic alkali salt, such as sodium hydroxide, sodium carbonate and/or potassium carbonate is preferred because of easy control of the reaction and low cost.

Furthermore, the process of cyanating using hydrocyanate includes, for example, reacting glycidol or 2-methyl-2,3-epoxypropanol with a hydrocyanate in a weak acidic solution such as aqueous magnesium sulfate solution or acetic acid. The hydrocyanate used in the reaction includes various metal salts, but inexpensive potassium cyanate and sodium cyanate are preferably used.

The reaction temperature for cyanation is preferably from about −20 to 70° C., and the reaction is performed, more preferably, at a temperature ranging from about −10 to 40° C. for the purpose of inhibiting the side reaction. The resulting 3,4-dihydroxybutanenitrile or 3,4-dihydroxy-3-methylbutanenitrile can be used in the following reaction without being purified, but may also be purified by a conventional process.

Then, the resulting 3,4-dihydroxybutanenitrile or 3,4-dihydroxy-3-methylbutanenitrile is hydrolyzed to obtain 3,4-dihydroxybutanoic acid or 3,4-dihydroxy-3-methylbutanoic acid. Hydrolysis can be performed under an acid or alkali condition, but the alkali condition is preferred in view of the yield. As an alkali used in the reaction, sodium hydroxide and potassium hydroxide are preferred because of low cost. The reaction temperature for hydrolysis is preferably from about 0 to 120° C., and more preferably from about 50 to 100° C. in view of the yield. The resulting alkali salt of 3,4-dihydroxybutanoic acid or 3,4-dihydroxy-3-methylbutanoic acid is neutralized by adding acid. As the acid used in this case, any mineral acid may be used.

Moreover, it is preferred to use inexpensive sulfuric acid and hydrochloric acid, and to use an acidic ion exchange resin which is easy to remove.

The 3,4-dihydroxybutanoic acid or 3,4-dihydroxy-3-methylbutanoic acid thus obtained is then lactonized to obtain -hydroxy-β-methyl-γ-butyrolactone or β-hydroxy-γ-butyrolactone. The lactonization reaction proceeds spontaneously in a typical concentration process, but may also be performed at about 0–100° C. under acidic condition. As the acid used in this case, any mineral acid may be used. However, it is preferred to use inexpensive sulfuric acid and/or hydrochloric acid, and to use an acidic ion exchange resin which is easy to remove. The resulting β-hydroxy-γ-butyrolactones may be purified by a conventional process, if necessary.

The process for preparing β-hydroxy-γ-butyrolactones, entailing cyanating glycidol or 2-methyl-2,3-epoxypropanol, followed by hydrolysis and then lactonization was described above with reference to each step, but these steps can also be performed in a single vessel without being purified according to the present invention. This means that the present invention also relates to a process capable of preparing β-hydroxy-γ-butyrolactones using a simple apparatus, without isolation and purification of intermediates, which is economically advantageous.

In the present invention, in order to obtain β-(meth) acryloyloxy-γ-butyrolactone and -β-methyl(meth) acryloyloxy-γ-butyrolactones represented by the formula (2), which are referred to as β-(meth)acryloyloxy-γ-butyrolactones, β-hydroxy-γ-butyrolactones obtained by the above process are esterified with (meth)acrylic acid chloride or (meth)acrylic acid, or ester-interchanged with (meth) acrylate. The β-(meth)acryloyloxy-γ-butyrolactones thus obtained may also be purified by a conventional process, if necessary.

When esterifying with (meth)acrylic acid chloride, a basic catalyst is usually used. The basic catalyst may be any one which is capable of neutralizing an acid produced and is not specifically limited. Examples examples thereof include triethylamine, pyridine and sodium hydrogencarbonate. The reaction temperature is usually from about −80 to 100° C., and is preferably controlled to about 0° C. or lower to inhibit side reactions, and more preferably from about −80 to −20° C.

When esterifying with (meth)acrylic acid, a condensing agent is usually used. The condensing agent may be any general condensing agent for esterification and is not specifically limited. Examples thereof include N,N'-dicyclohexylcarbodiimide, 2-chloro-1,3-dimethylimidazolium chloride and propanesulfonic anhydride. In this case, an amine base, such as 4-dimethylaminopyridine or triethylamine may be used in combination. The reaction temperature is usually from about −30 to 100° C., and is preferably about 0° C. or higher to obtain a significant reaction rate, and more preferably from about 15 to 40° C.

In the case of ester-interchanging with (meth) acrylate, a conventional catalyst for esterification is used. The catalyst used in the ester interchange may be a general catalyst for ester interchange reaction and is not specifically limited. Examples thereof include tetraalkoxytitaniums, such as tetrabutoxytitanium, tetraisopropoxytitanium and tetramethoxytitanium and dialkyltin oxides, such as dibutyltin oxide and dioctyltin oxide. The reaction temperature is usually from about −30 to 130° C., but is preferably from about 60 to 110° C. to remove alcohol as by-products by azeotropic distillation and to obtain a significant reaction rate.

That is, in the present invention, β-(meth) acryloyloxy-γ-butyrolactones are prepared by the chemical reaction scheme shown below.

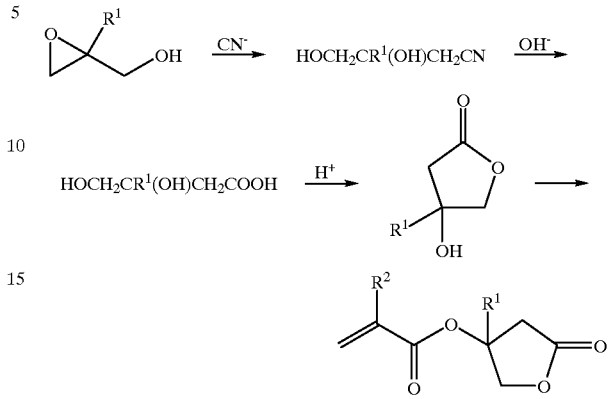

wherein $R^1$ and $R^2$ independently represent a hydrogen atom or a methyl group.

The present invention will now be further illustrated by certain Examples which are provided solely for illustration and are not intended to be limitative. Analysis in the Examples was performed by gas chromatography and NMR.

Purity was calculated from gas chromatographic peak area according to the following equation.

Purity (%)=(A/B)×100 where A represents a peak area of the desired product, and B represents the sum of a whole peak area.

Furthermore, actual yield was calculated according to the following equation.

Actual yield (%)=(C/D)×100 where C represents a mol number of the desired product, calculated by multiplying a weight of the desired product containing impurities by purity, followed by division by a molecular weight of the desired product, and D represents a mol number of a raw material as a basis.

EXAMPLE 1

Synthesis of β-hydroxy-γ-butyrolactone

To a glass flask equipped with a stirrer, a dropping funnel, a thermometer, a Dimroth condenser and an alkali trap of aqueous sodium hydroxide solution, magnesium sulfate heptahydrate (123.2 g, 0.5 mol), potassium cyanate (32.6 g, 0.5 mol) and 300 ml of water were added, and then glycidol (37.0 g, 0.5 mol) was added dropwise from the dropping funnel with ice cooling. After stirring 7 hours, an aqueous solution obtained by adding 50 ml of water to sodium hydroxide (25 g, 0.625 mol) was added dropwise and the mixture was heated at reflux at an internal temperature of 90 to 100° C. After about 1 hour, bubbles which are considered to be ammonia gas were observed. After heating for 16 hours, followed by air cooling and further ice cooling, concentrated hydrochloric acid (136 g, 1.35 mol) was added dropwise. This reaction solution was concentrated by using an evaporator and water was distilled off, thereby to deposit a large amount of a salt. To the salt, 1 liter of acetone and 50 g of magnesium sulfuric anhydride were added and, after filtering together with the salt, the filtrate was concentrated to obtain 55 g of crude-β-hydroxy-γ-butyrolactone. This β-hydroxy-γ-butyrolactone was purified by silica gel column chromatography to obtain β-hydroxy-γ-butyrolactone (34.8 g, 0.205 mol).

The purity of the resulting β-hydroxy-γ-butyrolactone was 98% and the actual yield was 40% (on the basis of glycidol) Spectrum data of $^1$H-NMR of the product were as follows.

$^1$H-NMR (CDCl$_3$): 2.5 (1H, d, J=18.1 Hz), 2.8 (1H, dd, J=5.9 Hz, 18.1 Hz), 3.5 (1H, br), 4.3 (1H, d, J=10.3 Hz), 4.4 (1H, dd, J=4.3 Hz, 10.3 Hz), 4.7 (1H, ddd, J=2.0 Hz, 4.3 Hz, 5.9 Hz)

EXAMPLE 2

Synthesis of β-hydroxy-γ-butyrolactone

In a 1 liter glass reaction vessel, glycidol (293.0 g, 3.8 mol), water (92.8 g, 5.2 mol) and potassium carbonate (8.7 g, 0.063 mol) were charged, and then a hydrocyanic acid gas (97.8 g, 3.6 mol) was fed with ice cooling over 10 hours. The reaction temperature was slowly raised within a range from 8 to 25° C. An aqueous solution obtained by adding 6.6 g of water to potassium carbonate (3.3 g, 0.024 mol) was added twice, followed by aging at room temperature for 2 days. To the resulting reaction solution containing 3,4-dihydroxybutanenitrile, 1200 ml of water and an aqueous solution obtained by adding 500 ml of water to sodium hydroxide (197 g, 4.93 mol) were added dropwise and the mixture was heated at reflux at an internal temperature of 90 to 100° C. After about 1 hour, bubbles which are considered to be ammonia gas were observed. After heating for 18 hours, followed by air cooling and further ice cooling, concentrated hydrochloric acid (592 g, 5.92 mol) was added dropwise. This reaction solution was concentrated by using an evaporator and water was distilled off, thereby to deposit a large amount of a salt.

To the salt, 1 liter of acetone and 100 9 of magnesium sulfuric anhydride were added and, after filtering together with the salt, the filtrate was concentrated to obtain 348 g of crude β-hydroxy-γ-butyrolactone. This β-hydroxy-γ-butyrolactone was purified by silica gel column chromatography to obtain β-hydroxy-γ-butyrolactone (212.1 g, 2.08 mol).

The purity of the resulting β-hydroxy-γ-butyrolactone was 98% and the actual yield was 51% (on the basis of glycidol) Spectrum data of $^1$H-NMR of the product were as follows.

$^1$H-NMR (CDCl$_3$): 2.5 (1H, d, J=18.1 Hz), 2.8 (1H, dd, J=5.9 Hz, 18.1 Hz), 3.5 (1H, br), 4.3 (1H, d, J=10.3 Hz), 4.4 (1H, dd, J=4.3 Hz, 10.3 Hz), 4.7 (1H, ddd, J=2.0 Hz, 4.3 Hz, 5.9 Hz)

EXAMPLE 3

Synthesis of β-methacryloyloxy-γ-butyrolactone

In a glass flask equipped with a stirrer, two dropping funnels, a thermometer and a Dimroth condenser, β-hydroxy-γ-butyrolactone (91.1 g, 0.875 mol) having a purity of 98% obtained by repeating the process of Example 1 and 500 ml of dry dichloromethane were charged, and then triethylamine (117.5 g, 1.16 mol) was charged in one dropping funnel and methacrylic acid chloride (112 g, 1.071 mol) was charged in another dropping funnel. The atmosphere in the glass flask was replaced by nitrogen and then cooled to −60 to −70° C. in a dry ice-acetone bath. While stirring in the glass flask, triethylamine and methacrylic acid chloride were added dropwise with adjusting so that the amount of triethylamine becomes small excess to that of methacrylic acid chloride. After the completion of the dropwise addition, stirring was continued for 3 hours. To the reaction solution, 300 ml of water was added and a small amount of Celite was added, followed by filtration. The filtrate was washed three times with 300 ml of water using a separatory funnel and dried by adding 80 g of magnesium sulfate and, after filtering, the filtrate was concentrated to obtain 175 g of crude β-methacryloyloxy-γ-butyrolactone. This β-methacryloyloxy-γ-butyrolactone was purified by silica gel column chromatography to obtain β-methacryloyloxy-γ-butyrolactone (106.3 g, 0.625 mol).

The purity of the resulting β-methacryloyloxy-γ butyrolactone was 97% and the actual yield was 69% (on the basis of β-hydroxy-γ-butyrolactone) Spectrum data of $^1$H-NMR of the product were as follows.

$^1$H-NMR(CDCl$_3$): 2.1 (3H, s), 2.8 (1H, d, J=18.4 Hz), 3.0 (1H, dd, J=6.8 Hz, 18.4 Hz), 4.5 (1H, d, J=10.8 Hz), 4.7 (1H, dd, J=4.8 Hz, 10.8 Hz), 5.6 (1H, dd, J=4.8 Hz, 6.8 Hz), 5.8 (1H, s), 6.3 (1H, s)

According to the process of the present invention, β-hydroxy-γ-butyrolactones can be produced in a safe and simple manner. Furthermore, by using β-hydroxy-γ-butyrolactones obtained by the present invention, β-(meth)acryloyloxy-γ-butyrolactones, which are useful as a constituent component monomer of paints, adhesives, sticking agents, and resins for ink, for example, can be produced.

Having described the present invention, it will be apparent that many changes and modifications may be made to the above-described embodiments without departing from the spirit and the scope of the present invention.

What is claimed is:

1. A process for preparing β-hydroxy-γ-butyrolactone or β-methyl-β-hydroxy-γ-butyrolactone having the formula (1):

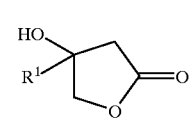

wherein R$^1$ is a hydrogen or methyl, which comprises (a) cyanating glycidol or 2-methyl-2,3-epoxypropanol, b) hydrolyzing the product of step a), and c) lactonizing the product of step b).

2. The process of claim 1, wherein said step a) is effected by reacting glycidol or 2-methyl-2,3-epoxypropanol with hydrocyanic acid in the presence of a basic catalyst.

3. The process of claim 2, wherein said basic catalyst is an inorganic alkali salt.

4. The process of claim 3, wherein said inorganic alkali salt is sodium hydroxide, sodium carbonate or potassium carbonate.

5. The process of claim 1, which is effected at a temperature of about −20° to −70° C.

6. The process of claim 5, which is effected at a temperature of about −10° to 40° C.

7. The process of claim 1, wherein said step a) is effected by reacting glycidol or 2-methyl-2,3-epoxypropanol with metal hydrocyanate in the presence of acidic solution.

8. The process of claim 7, wherein said metal hydrocyanate is potassium cyanate or sodium cyanate.

9. The process of claim 7, wherein said acidic solution is acetic acid or magnesium sulfate solution.

10. The process of claim 1, wherein said step b) is effected under alkaline or acidic conditions.

11. The process of claim 10, wherein said step b) is effected under alkaline conditions.

12. The process of claim 10, wherein said step b) is effected at from about 0° to 120° C.

13. The process of claim 12, wherein said step b) is effected at from about 50 to 100° C.

14. The process of claim 1, wherein said step c) is effected at about 0° to 100° C. under acidic conditions.

15. The process of claim 14, wherein said acidic conditions are effected using mineral acid.

16. The process of claim 14, wherein said acid conditions are effected using acidic ion exchange resin.

17. The process of claim 1, which is conducted in a single vessel without isolating any intermediates.

18. A process for preparing β-(meth)acryloyloxy-γ-butyrolactone or β-methyl(meth)acryloyloxy-γ-butyrolactone having the formula (2):

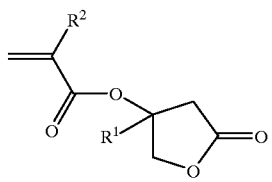

(2)

wherein $R^1$ and $R^2$ are each independently hydrogen or methyl, which comprises a) cyanating glycidol or 2-methyl-2,3-epoxypropanol, b) hydrolyzing the product of step a), c) lactonizing the product of step b), and d) esterifying the product of step c) with (meth)acrylic acid chloride, (meth)acrylic acid or (meth)acrylic ester.

19. The process of claim 18, wherein the product of step c) is esterified with (meth)acrylic acid chloride in the presence of a basic catalyst.

20. The process of claim 19, wherein said basic catalyst is pyridine, triethylamine or sodium hydrogencarbonate.

21. The process of claim 18, which is conducted at a temperature of from about −80° to 0° C.

22. The process of claim 21, which is conducted at a temperature of from −80° to 0° C.

23. The process of claim 18, wherein the product of step c) is esterified with (meth)acrylic acid in the presence of a condensing agent.

24. The process of claim 23, wherein the condensing agent is selected from the group consisting of N,N'-dicyclohexylcarbodiimide, 2-chloro-1,3-dimethylimidazolium chloride, and propanesulfonic anhydride.

25. The process of claim 23, which is conducted at a temperature of from about −30° to 100° C.

26. The process of claim 25, which is conducted at a temperature of from about 0 ° to 100° C.

27. The process of claim 18, wherein the product of step c) is esterfied by ester-interchange with (meth) acrylic ester in the presence of an ester-interchange catalyst.

28. The process of claim 27, wherein said ester-interchange catalyst is tetra alkoxytitaniums or dialkyltin oxides or a combination thereof.

29. The process of claim 27, which is conducted at a temperature of from −30° to 130° C.

30. The process of claim 29, which is conducted at a temperature of from 60° to 110° C.

* * * * *

UNITED STATES PATENT AND TRADEMARK OFFICE
CERTIFICATE OF CORRECTION

| | | |
|---|---|---|
| PATENT NO. | : 6,313,321 B1 | Page 1 of 1 |
| DATED | : November 6, 2001 | |
| INVENTOR(S) | : Murata et al. | |

It is certified that error appears in the above-identified patent and that said Letters Patent is hereby corrected as shown below:

Title page,
Item [54], and at the top of column 1, the title should read:

-- [54] PROCESS FOR PREPARING β-HYDROXY-γ-BUTYROLACTONES AND β-(METH) ACRYLOYLOXY-γ-BUTYROLACTONES --

Item [30], the Foreign Application Priority Data should read:

-- [30]        Foreign Application Priority Data
    Dec. 25, 1997   (JP) ............................................. 9-357715 --

Signed and Sealed this

Twelfth Day of March, 2002

*Attest:*

*Attesting Officer*

JAMES E. ROGAN
*Director of the United States Patent and Trademark Office*